United States Patent
Roberts

(10) Patent No.: US 6,740,646 B2
(45) Date of Patent: May 25, 2004

(54) BIOAVAILABLE PRODRUGS OF ANDROGENIC STEROIDS AND RELATED METHOD

(75) Inventor: William J. Roberts, Gainesville, FL (US)

(73) Assignee: Biotest Laboratories, LLC, Colorado Springs, CO (US)

( * ) Notice: Subject to any disclaimer, the term of this patent is extended or adjusted under 35 U.S.C. 154(b) by 0 days.

(21) Appl. No.: 10/053,345

(22) Filed: Jan. 16, 2002

(65) Prior Publication Data

US 2003/0134830 A1 Jul. 17, 2003

(51) Int. Cl.$^7$ .............. A61K 31/568; C07J 1/00
(52) U.S. Cl. .............. 514/178; 514/182; 552/633
(58) Field of Search .............. 552/633; 514/178, 514/182

(56) References Cited

U.S. PATENT DOCUMENTS

| | | |
|---|---|---|
| 2,843,608 A | 7/1958 | Colton |
| 3,056,727 A | 10/1962 | Allais et al. |
| 3,314,856 A | 4/1967 | Allais et al. |
| 3,433,813 A | 3/1969 | Boswell |
| 3,435,030 A | 3/1969 | Kimstra |
| 3,481,957 A | 12/1969 | Cross et al. |
| 3,523,126 A | 8/1970 | Boswell |
| 4,087,524 A | 5/1978 | Grunwell et al. |
| 4,239,681 A | 12/1980 | Grunwell et al. |
| 5,053,403 A | 10/1991 | Orentreich et al. |
| 5,387,583 A | 2/1995 | Loria |
| 5,391,776 A | 2/1995 | Ueno et al. |
| 5,578,588 A | 11/1996 | Mattern et al. |
| 5,622,944 A | 4/1997 | Hale et al. |
| 5,880,117 A | 3/1999 | Arnold |
| 6,011,027 A | 1/2000 | Arnold |
| 6,017,964 A | 1/2000 | MacLean et al. |
| 6,117,429 A | 9/2000 | Bucci |
| 2001/0041698 A1 | 11/2001 | Arnold |
| 2001/0056087 A1 | 12/2001 | Arnold |
| 2002/0183532 A1 | 12/2002 | Roberts |

FOREIGN PATENT DOCUMENTS

| BE | 636216 | 8/1963 |

OTHER PUBLICATIONS

Ohloff et al., "Structural and Configurational Dependence of the Sensory Process in Steroids." Helvetica Chimica Acta, vol. 66(1), pp. 192–217, 1983.*

Marwah, P. et al., "Ergosteroids IV: Synthesis and Biological Acitivity of Steroid Glucuronosides, Ethers, and Alkylcarbonates," Steroids, 2001, pp. 581–595, vol. 66, Elsevier.

Blaquier et al., "In Vitro Metabolism of Androgens in Whole Human Blood", Acta Endocrinologica, May–Aug. 1967, 697–704, vol. 55, Periodica, Copenhagen.

Earnest et al., "In Vivo 4–androstene–3,17–dione and 4–androstene–3β, 17β–diol Supplementation in Young Men", European Journal of Applied Physiology, Feb. 2000, 229–232, vol. 81, No. 3, Springer, New York.

Franke et al., "Hormonal Doping and Androgenization of Athletes: A Secret Program of the German Democratic Republic Government", Clinical Chemistry, Nov. 7, 1997, 1262–1279, vol. 43, No. 7, American Association for Clinical Chemistry, United States of America.

Inaba et al., "Conversion of 4–Androstenediol and 5–Androstenediol to Testosterone, and Conversion of Dehydroepiandrosterone to 4–Anderostenediol by Rat Testis In Vitro", Endocrinol. Jun. 1966, 160–172, vol. 13, No. 2, Japan.

Uralets et al., "Over–the–Counter Anabolic Steroids 4–Androsten–3, 17–dione; 4–Androsten3β, 17β–diol; and 19–nor–4–Androsten–3, 17–dione: Excretion Studies in Men", Journal of Analytical Toxicology, Sep. 1999, 357–366, vol. 23, : Preston Publications, Niles, Illinois.

Yamaji et al., "Androstenediol in Canine Spermatic Vein Blood and Its Significance In Testosterone Biosynthesis in Vivo", Endocrinology, 1968, 992–998, vol. 83, J. B. Lippincott, Philadelphia.

* cited by examiner

*Primary Examiner*—Barbara P. Badio
(74) *Attorney, Agent, or Firm*—Sullivan Law Group

(57) ABSTRACT

A compound is provided for increasing the concentration of a parent androgen in a subject in vivo. The parent androgen has a skeletal structure including a 1 position and a 17 position, a 17β-hydroxy group comprising a 17β-hydroxy oxygen appended to the 17 position, and a 17β-hydroxy hydrogen appended to the 17β-hydroxy oxygen. The compound includes a substrate having the skeletal structure of the parent androgen. It includes a 1 position and a 17 position corresponding to the 1 and 17 positions respectively of the parent androgen. The substrate has a carbon—carbon double bond at the 1 position. The compound also has a promoiety appended to the 17β-hydroxy oxygen of the substrate as a substitute for the 17β-hydroxy hydrogen of the parent androgen. The promoiety includes, and preferably consists of, an alkylcarbonate ester. A related method also is provided.

40 Claims, No Drawings

BIOAVAILABLE PRODRUGS OF ANDROGENIC STEROIDS AND RELATED METHOD

BACKGROUND OF THE INVENTION

1. Field of the Invention

The present invention pertains to the field of biochemistry and more specifically to the field of prodrugs or prohormones of androgenic steroids and related methods.

2. Description of the Related Art

The importance of having sufficient concentrations of androgenic steroids in the body is well known. The advantages of such steroids can include such things as increased physical performance, improved body composition or increased density, and increased sexual drive or performance, depending upon the specific steroid, organism, etc. It is equally well known that under many common circumstances, deficiencies of these androgenic steroids arise. In humans, for example, as one ages, the normal concentrations of these steroids tend to decrease. Men over the age of about thirty-five typically suffer a reduction in the blood serum concentration of free testosterone. These changes typically result in a reduced general athletic performance and longer time requirements for restoration after extensive exercise, as well as reduced physical and psychological resistance to stress.

A known approach to addressing such steroid concentration deficiencies is to introduce the deficient steroid into the body. In U.S. Pat. No. 5,578,588, for example, methods are disclosed for delivering testosterone supplements including peroral administration or intramuscular injection of testosterone.

This approach, however, suffers from a number of disadvantages. Introduction of such steroid supplements has been associated with undesirable effects such as poor control over blood concentrations and loss of the steroid due to a "first pass effect," wherein the steroid is metabolized by the liver prior to reaching general circulation. These losses dramatically reduce the available steroid and, consequently, much higher doses of the steroid supplement generally must be administered to achieve the desired effects. The higher doses sometimes result in an undesirable and unpredictable rise in overall steroid concentration, which, for example, in the case of testosterone, can result in physiological and psychological problems.

Another approach to addressing steroid concentration deficiencies is to introduce a prodrug of the steroid into the body. An example of a prodrug is a prohormone. A prohormone is a compound that itself has no anabolic activity but, when administered in the body, is metabolized or converted into a natural or desired hormone. Such prohormones become substrates for in vivo bioconversion into the parent compounds, i.e., the corresponding natural or desired hormones. U.S. Pat. No. 5,053,403, for example, discloses that specific prohormones including androstenedione, progesterone, and 17α-β derivatives or analogues can be administered to humans for the purpose of increasing blood concentration of testosterone, with fewer undesirable effects. Long term use of these prohormones, however, is also associated with side effects, such as gynecomastia. A pernasal dose of 3.5 mg to 15 mg of these prohormones is reported to increase the blood concentration of testosterone by 34% to 97%. Similarly, U.S. Pat. No. 5,880,117 discloses the use of 4-androstenediol as a peroral testosterone supplement. Androstenedione is a direct precursor of testosterone and estrogen in target tissues having appropriate receptors and enzymes. According to U.S. Pat. No. 6,117,429, androstenediols are precursors for testosterone after oral administration in adults. 19-norandrostenedione is a precursor for 19-nortestosterone, which has a similar anabolic activity in comparison to testosterone.

The general approach of using prodrugs or prohormones to achieve supplementation of androgenic steroid concentrations in vivo also has been limited, however, in that the effectiveness of such compounds has tended to be low. In some instances, their conversion into the desired steroid is limited, for example, because they are removed from the system through the first pass effect. They also can be converted into undesirable products, for example, as in the case wherein 4-androstenedione is converted into estrogen. Even where the desired bioconversion occurs, the rate of conversion can be sufficiently low that undesirably large quantities of the prodrug must be taken to achieve desired results. This itself can have undesirable side effects.

It is advantageous in many instances to have a prodrug that may be administered in a convenient form, such as by oral, sublingual or pernasal administration. Many prodrugs have not been amenable to such administration, however, because they tend to be broken down prior to absorption in vivo when administered in this fashion.

OBJECTS OF THE INVENTION

Accordingly, an object of the present invention is to provide compositions and methods that can be used to increase the in vivo concentration and bioavailability of a parent androgen.

Another object of the invention according to certain aspects is to provide compounds and methods that can be used to increase the in vivo concentration and bioavailability of a parent androgen with while being amenable to convenient administration, such as by oral, sublingual or pernasal administration.

Additional objects and advantages of the invention will be set forth in the description that follows, and in part will be apparent from the description, or may be learned by practice of the invention. The objects and advantages of the invention may be realized and obtained by means of the instrumentalities and combinations pointed out in the appended claims.

SUMMARY OF THE INVENTION

To achieve the foregoing objects, and in accordance with the purposes of the invention as embodied and broadly described in this document, a compound is provided for increasing the concentration of a parent androgen in a subject in vivo, wherein the parent androgen has a skeletal structure including a 1 position and a 17 position and the parent androgen further has a 17β-hydroxy group comprising a 17β-hydroxy oxygen appended to the 17 position and a 17β-hydroxy hydrogen appended to the 17β-hydroxy oxygen.

The compound according to this aspect of the invention comprises a substrate having the skeletal structure of the parent androgen comprising a 1 position and a 17 position corresponding to the 1 and 17 positions respectively of the parent androgen. The substrate further comprises a carbon—carbon double bond at the 1 position. The compound also comprises a promoiety appended to the 17 position of the substrate as a substitute for the 17β-hydroxy hydrogen of the parent androgen. The promoiety comprises an alkylcarbonate ester.

The substrate has the skeletal structure of the parent androgen, preferably wherein the parent androgen is selected from the group consisting of 5α-androst-1-ene-3α, 17β-diol, 5α-androst-1-ene-3β, 17β-diol, and mixtures thereof. The substrate also may have the skeletal structure of the parent androgen wherein the parent androgen is selected from the group consisting of 5α-estr-1-ene-3α, 17β-diol, 5α-estr-1-ene-3β, 17β-diol, and mixtures thereof. In addition, the parent androgen to which the substrate corresponds may comprise 17β-hydroxy-5α-androst-1-ene-3-one. The substrate still further may have the skeletal structure of the parent androgen wherein the parent androgen is selected from the group consisting of 17β-hydroxyandrost-1,4-diene-3-one, 17β-hydroxyestr-1,4-diene-3-one, 17β-hydroxy-5α-estr-1-ene-3-one, and mixtures thereof.

The alkylcarbonate ester optionally but preferably has an alkyl chain length of less than 12, and more preferably of less than 11. The alkylcarbonate ester may be selected from the group consisting of methyl carbonate, ethyl carbonate, propyl carbonate, isopropyl carbonate, butyl carbonate, isobutyl carbonate, t-butyl carbonate, valeryl carbonate, hexyl carbonate, heptyl carbonate, octyl carbonate, nonyl carbonate, decyl carbonate, undecyl carbonate, dodecyl carbonate, cyclopentyl carbonate, cyclopentylmethyl carbonate, cyclopentylpropyl carbonate, cyclohexylmethyl carbonate, cyclohexylpropyl carbonate, and mixtures thereof. The compound itself according to this aspect of the invention may assume a number of specific forms. It may, for example, comprise 17β-hydroxy-5α-androst-1-ene-3-one 17β-alkylcarbonate, 17β-hydroxy-5α-androst-1-ene-3-one 17β-ethylcarbonate, 17β-hydroxyandrost-1,4-diene-3-one 17β-alkycarbonate, or 17β-hydroxyandrost-1,4-diene-3-one 17β-ethylcarbonate. It also may take the form of mixtures or combinations of these. Incidentally, compounds identified or referred to herein that identify a bond or functional group at the 3 position, e.g., those identified in this paragraph, may comprise a 3α or a 3β unless indicated otherwise.

The compound also may take the form of estranes and derivatives, such as ketone derivatives. It may, for example, comprise 17β-hydroxy-5α-estr-1-ene-3-one 17β-alkylcarbonate, 17β-hydroxyestr-1,4-diene-3-one 17β-alkycarbonate, and like forms. The ethyl carbonates are preferred forms of the alkylcarbonate promoiety in such molecules, e.g., 17β-hydroxy-5α-estr-1-ene-3-one 17β-ethylcarbonate.

Compounds according to this aspect of the invention also may comprise diols. Examples would include 5α-androst-1-ene-3-ol 17β-alkylcarbonate, 5α-androst-1-ene-3,17β-diol 17β-alkylcarbonate (e.g., 5α-androst-1-ene-3,17β-diol 17β-ethylcarbonate), 5α-androst-1-ene-3,17β-diol-3,17β-di(alkylcarbonate) (e.g.,5α-androst-1-ene-3,17β-diol-3,17β-di(ethylcarbonate)), and similar forms.

In some forms, particularly those intended for peroral administration, it is preferable albeit optional for the compound to include a carrier. The carrier may be a solid, a liquid, a semi-solid, or other suitable form.

In accordance with another aspect of the invention, a method is provided for increasing the concentration of a parent androgen in a subject in vivo, wherein the parent androgen has a skeletal structure including a 1 position and a 17 position and the parent androgen further has a 17β-hydroxy group comprising a 17β-hydroxy oxygen appended to the 17 position and a 17β-hydroxy hydrogen appended to the 17β-hydroxy oxygen.

The method according to this aspect of the invention comprises administering to the subject a compound comprising a substrate and a promoiety. The substrate has the skeletal structure of the parent androgen comprising a 1 position and a 17 position corresponding to the 1 and 17 positions respectively of the parent androgen, and the substrate comprises a carbon—carbon double bond at the 1 position. The promoiety is appended to the 17 position of the substrate as a substitute for the 17β-hydroxy hydrogen of the parent androgen, and comprises an alkylcarbonate ester. The method further comprises converting the compound in vivo into the parent androgen. The subject may be a human being, in which case the in vivo conversion comprises converting the compound into the parent androgen in vivo within the human being.

In accordance with this aspect of the invention, the skeletal structure of the parent androgen to which the substrate corresponds may be selected from the group consisting of 5α-androst-1-ene-3α,17β-diol, 5α-androst-1-ene-3β,17β-diol, and mixtures thereof. It also may be selected from the group consisting of 5α-estr-1-ene-3α,17β-diol, 5α-estr-1-ene-3β, 17β-diol, and mixtures thereof. The skeletal structure of the parent androgen to which the substrate corresponds also may comprise 17β-hydroxy-5α-androst-1-ene-3-one. It also may be selected from the group consisting of 17β-hydroxyandrost-1,4-diene-3-one, 17β-hydroxyestr-1,4-diene-3-one, 17β-hydroxy-5α-estr-1-ene-3-one, and mixtures thereof.

The alkylcarbonate ester promoiety may be as described above. It may, for example, be selected from the group consisting of methyl carbonate, ethyl carbonate, propyl carbonate, isopropyl carbonate, butyl carbonate, isobutyl carbonate, t-butyl carbonate, valeryl carbonate, hexyl carbonate, heptyl carbonate, octyl carbonate, nonyl carbonate, decyl carbonate, undecyl carbonate, dodecyl carbonate, cyclopentylmethyl carbonate, cyclopentyl carbonate, cyclopentylpropyl carbonate, cyclohexylmethyl carbonate, cyclohexylpropyl carbonate, and mixtures thereof.

In accordance with this method aspect, the administered compound may comprise 17β-hydroxy-5α-androst-1-ene-3-one 17β-alkylcarbonate (e.g., 17β-hydroxy-5α-androst-1-ene-3-one 17β-ethylcarbonate), 17β-hydroxyandrost-1,4-diene-3-one 17β-alkycarbonate (e.g., 17β-hydroxyandrost-1,4-diene-3-one 17β-ethylcarbonate), 17β-hydroxy-5α-estr-1-ene-3-one 17β-alkylcarbonate (e.g., 17β-hydroxy-5α-estr-1-ene-3-one 17β-ethylcarbonate), and/or 17β-hydroxyestr-1,4-diene-3-one 17β-alkycarbonate (e.g., 17β-hydroxyestr-1,4-diene-3-one 17β-ethylcarbonate).

The compound to be administered may comprise diols, for example, such as 5α-androst-1-ene-3,17β-diol 17β-alkylcarbonate (e.g., 5α-androst-1-ene-3,17β-diol 17β-ethylcarbonate), 5α-androst-1-ene-3,17β-diol-3,17β-di(alkylcarbonate) (e.g., 5α-androst-1-ene-3, 17β-diol-3,17β-di(ethylcarbonate), and mixtures thereof.

The compound administration may comprise peroral administration, pernasal administration, transdermal administration, sublingual administration, and other means. Peroral administration is presently preferred.

As part of the method, the compound administration may comprise complexing the compound with an hydroxypropyl beta cyclodextrin, and/or with an hydroxypropyl gamma cyclodextrin.

Also as part of the compound administration according to this aspect of the invention, the compound preferably is administered once per day, although this is not limiting and other dosage regiments may be preferred depending upon the specific compound, the subject, etc. The compound may be administered in a dosage periodically for a maximum of two weeks, followed by at least two weeks of non-administration to permit recovery of natural parent androgen production in the subject.

The compound administration optionally but preferably comprises administering the compound in an amount ranging from 1.0 mg to 1 gram per day. More preferably, the compound administration comprises administering the compound in an amount ranging from 50 mg to 500 mg per day, and even more preferably in an amount ranging from 100 mg to 400 mg per day.

The compound administration optionally may further include applying an enteric coating to the compound prior to administering the compound.

DETAILED DESCRIPTION OF THE PREFERRED EMBODIMENTS AND METHODS

Reference will now be made in detail to the presently preferred embodiments and methods of the invention. It should be noted, however, that the invention in its broader aspects is not limited to the specific details, representative compositions and methods, and illustrative examples described in this section in connection with the preferred embodiments and methods. The invention according to its various aspects is particularly pointed out and distinctly claimed in the attached claims read in view of this specification, and appropriate equivalents.

In accordance with one aspect of the invention, a compound is provided for increasing the concentration of a parent androgen in a subject in vivo. As noted above, the parent androgen has a skeletal structure including a 1 position and a 17 position. This numbering corresponds to the ring identification and carbon numbering system well known in the field of steroid chemistry, for example, as adopted in the 1989 recommendations of the International Union of Pure and Applied Chemistry ("IUPAC"). The parent androgen also has a 17β-hydroxy group comprising a 17β-hydroxy oxygen appended to the 17 position and a 17β-hydroxy hydrogen appended to the 17β-hydroxy oxygen.

The compound preferably but optionally is for treatment of a human being to supplement or increase the concentration of the parent androgen in vivo. This is not necessarily limiting, however, and veterinary applications also are possible in certain instances.

In accordance with this aspect of the invention, the compound comprises a substrate and a promoiety. The substrate has the skeletal structure of the parent androgen. It comprises a 1 position and a 17 position corresponding to the 1 and 17 positions respectively of the parent androgen. The substrate comprises a carbon—carbon double bond at the 1 position.

The skeletal structure of the parent androgen to which the substrate corresponds may take a number of forms. It may, for example, be selected from the group consisting of 5α-androst-1-ene-3α,17β-diol, 5α-androst-1-ene-3β,17β-diol, and mixtures thereof. It also may be selected from the group consisting of 5α-estr-1-ene-3α,17β-diol, 5α-estr-1-ene-3β,17β-diol, and mixtures thereof. In addition, it may be selected from the group consisting of 17β-hydroxyandrost-1,4-diene-3-one 17β-hydroxyestr-1,4-diene-3-one, 5α,17β-hydroxyestr-1-ene-3-one, and mixtures thereof. This skeletal structure may comprise, for example, 17β-hydroxy-5α-androst-1-ene-3-one.

The promoiety is appended to the 17β-hydroxy oxygen of the substrate as a substitute for the 17β-hydroxy hydrogen.

It comprises and preferably consists of an alkylcarbonate ester. The alkyl group may be linear, branched, cyclical, etc. The promoiety preferably but optionally has an alkyl chain length (counting only the carbon atoms) of less than 12, and more preferably of less than 11. The alkylcarbonate ester may be selected from the group consisting of methyl carbonate, ethyl carbonate, propyl carbonate, isopropyl carbonate, butyl carbonate, isobutyl carbonate, t-butyl carbonate, valeryl carbonate, hexyl carbonate, heptyl carbonate, octyl carbonate, nonyl carbonate, decyl carbonate, undecyl carbonate, dodecyl carbonate, cyclopentyl methyl carbonate, cyclopentylpropyl carbonate, cyclohexyl methyl carbonate, cyclohexylpropyl carbonate, and mixtures thereof. Other alkyl carbonate esters, however, may be used. Alkyl carbonate esters having lower carbon chain lengths generally are preferred, although not universally so. Ethylcarbonate esters generally are even more preferred.

The compound according to this aspect of the invention in its presently preferred embodiments may comprise 17β-hydroxy-5α-androst-1-ene-3-one 17β-alkylcarbonate, 17β-hydroxyandrost-1,4-diene-3-one 17β-alkycarbonate. The ethyl carbonate esters, e.g., 17β-hydroxy-5α-androst-1-ene-3-one 17β-ethylcarbonate, and 17β-hydroxyandrost-1,4-diene-3-one 17β-ethylcarbonate, again, would be preferred.

The compound also may comprise estranes, for example, such as 17β-hydroxy-5α-estr-1-ene-3-one 17β-alkylcarbonate, 17β-hydroxyestr-1,4-diene-3-one 17β-alkycarbonate, and their ethylcarbonate embodiments such as 17β-hydroxy-5α-estr-1-ene-3-one 17β-ethylcarbonate. The compound also may comprise diols. Illustrative examples would include 5α-androst-1-ene-3,17β-diol 17β-alkylcarbonate (e.g., 5α-androst-1-ene-3,17β-diol 17β-ethylcarbonate), and 5α-androst-1-ene-3,17β-diol-3,17β-di(alkylcarbonate), (e.g., 5α-androst-1-ene-3,17β-diol-3,17β-di(ethylcarbonate).

The principles of the invention according to this aspect also may be applied to dienes. Illustrative examples might include androst-1,4-diene-3α,17β-diol 17β-alkylcarbonate (e.g., androst-1,4-diene-3α,17β-diol 17β-ethylcarbonate), androst-1,4-diene-3β,17β-diol 17β-alkylcarbonate (e.g., androst-1,4-diene-3β,17β-diol 17β-ethylcarbonate), androst-1,4-diene-3β,17β-diol-3-alkylcarbonate (e.g., androst-1,4-diene-3β,17β-diol-3-ethylcarbonate), androst-1,4-diene-3,17β-diol-3,17β-di(alkylcarbonate) (e.g., androst-1,4-diene-3β,17β-diol-3,17β-di(ethylcarbonate), and mixtures of these.

The compound may be contained or encapsulated by an enteric coating. The compound also may be administered with a carrier, which may comprise a solid carrier, a semi-solid carrier, or a liquid carrier. A preferred liquid carrier is an aqueous emulsion including fatty acid ethyl esters, polysorbate 60, lecithin, and cholesterol or an oil. Another preferred liquid carrier comprises water, glycerin, polysorbate, lecithin, sodium benzoate, ethylene diamine tetraacetic acid ("EDTA"), potassium sorbate, grapefruit seed extract, and vegetable gum.

The compound according to this aspect of the invention may and preferably does comprise combinations of compounds having the alkylcarbonate ester promoiety as described herein. As noted, in each instance in this document wherein a group is bonded at the 3 position (at the first or "A" carbon ring), the 3 position configuration may comprise or consist essentially of either the α configuration or the β, and preferably both. In addition, stereochemistry at the 5 position for compounds other than 4-ene compounds preferably comprise 5α.

In accordance with another aspect of the invention, a compound is provided for increasing the concentration of a parent androgen in a subject in vivo, wherein the parent androgen has a skeletal structure including a 4 position and a 17 position. The parent androgen also has a 17β-hydroxy group comprising a 17β-hydroxy oxygen appended to the 17 position and a 17βhydroxy hydrogen appended to the 17β-hydroxy oxygen.

The compound according to this aspect of the invention comprises a substrate having the skeletal structure of the parent androgen comprising a 4 position and a 17 position corresponding to the 4 and 17 positions respectively of the parent androgen. The substrate comprises a carbon—carbon double bond at the 4 position. The compound further comprises a promoiety appended to the 17 position of the substrate as a substitute for the hydroxy hydrogen of the parent androgen. The promoiety comprises an alkylcarbonate ester.

The skeletal structure of the parent androgen to which the substrate corresponds may, for example, be selected from the group consisting of androst-4-ene-3α,17β-diol, androst-4-ene-3β,17β-diol, and mixtures thereof. It also may be selected from the group consisting of estr-4-ene-3α,17β-diol, estr-4-ene-3β,17β-diol, and mixtures thereof.

The aspects of the alkylcarbonate ester promoiety as noted with respect to the previous aspect of the invention apply here as well.

Preferred but merely illustrative compounds according to this aspect of the invention may comprise various forms of diols, for example, such as androst-4-ene-3,17β-diol 17β-alkylcarbonate (e.g., androst-4-ene-3,17β-diol 17β-ethylcarbonate), androst-4-ene-3,17β-diol-3,17β-di(alkylcarbonate) (androst-4-ene-3,17β-diol-3,17β-di(ethylcarbonate)), estr-4-ene-3,17β-diol 17β-alkylcarbonate (e.g., estr-4-ene-3,17β-diol 17β-ethylcarbonate, estr-4-ene-3,17β-diol-3,17β-di(alkylcarbonate) (e.g., estr-4-ene-3,17β-diol-3,17β-di(ethylcarbonate)).

The compound according to this aspect of the invention also may comprise a carrier, such as those forms noted above.

In accordance with another aspect of the invention, a method is provided for increasing the concentration of a parent androgen in a subject in vivo, wherein the parent androgen has a skeletal structure including a 1 position and a 17 position and the parent androgen further has a 17β-hydroxy group comprising a 17β-hydroxy oxygen appended to the 17 position and a 17β-hydroxy hydrogen appended to the 17β-hydroxy oxygen.

The method according to this aspect of the invention comprises administering to the subject a compound comprising a substrate and a promoiety. The substrate has the skeletal structure of the parent androgen comprising a 1 position and a 17 position corresponding to the 1 and 17 positions respectively of the parent androgen, and the substrate comprises a carbon—carbon double bond at the 1 position. The promoiety is appended to the 17 position of the substrate as a substitute for the 17β-hydroxy hydrogen of the parent androgen, and comprises an alkylcarbonate ester.

In accordance with this aspect of the invention, the skeletal structure of the parent androgen to which the substrate corresponds may be selected from the group consisting of 5α-androst-1-ene-3α,17β-diol, 5α-androst-1-ene-3β,17β-diol, and mixtures thereof. It also may be selected from the group consisting of 5α-estr-1-ene-3α,17β-diol, 5α-estr-1-ene-3β,17β-diol, and mixtures thereof. The skeletal structure of the parent androgen to which the substrate corresponds also may comprise 17β-hydroxy-5α-androst-1-ene-3-one. It also may be selected from the group consisting of 17β-hydroxyandrost-1,4-diene-3-one, 17β-hydroxyestr-1,4-diene-3-one, 17β-hydroxy-5α-estr-1-ene-3-one, and mixtures thereof.

The alkylcarbonate ester promoiety may be as described above. It may, for example, be selected from the group consisting of methyl carbonate, ethyl carbonate, propyl carbonate, isopropyl carbonate, butyl carbonate, isobutyl carbonate, t-butyl carbonate, valeryl carbonate, hexyl carbonate, heptyl carbonate, octyl carbonate, nonyl carbonate, decyl carbonate, undecyl carbonate, dodecyl carbonate, cyclopentyl carbonate, cyclopentylmethyl carbonate, cyclopentylpropyl carbonate, cyclohexylmethyl carbonate, cyclohexylpropyl carbonate, and mixtures thereof.

In accordance with this method aspect, the administered compound may comprise 17β-hydroxy-5α-androst-1-ene-3-one 17β-alkylcarbonate (e.g., 17β-hydroxy-5α-androst-1-ene-3-one 17β-ethylcarbonate), 17β-hydroxyandrost-1,4-diene-3-one 17β-alkycarbonate (e.g., 17β-hydroxyandrost-1,4-diene-3-one 17β-ethylcarbonate), 17β-hydroxy-5α-estr-1-ene-3-one 17β-alkylcarbonate (e.g., 17β-hydroxy-5α-estr-1-ene-3-one 17β-ethylcarbonate), and/or 17β-hydroxyestr-1,4-diene-3-one 17β-alkycarbonate (e.g., 17β-hydroxyestr-1,4-diene-3-one 17β-ethylcarbonate).

The compound to be administered may comprise diols, for example, such as 5α-androst-1-ene-3,17β-diol 17β-alkylcarbonate (e.g., 5α-androst-1-ene-3,17β-diol 17β-ethylcarbonate), 5α-androst-1-ene-3,17β-diol 3,17β-di(alkylcarbonate) (e.g., 5α-androst-1-ene-3,17β-diol 3,17β-di(ethylcarbonate).

In accordance with another aspect of the invention, a method is provided for increasing the concentration of a parent androgen in a subject in vivo, again, wherein the parent androgen has a skeletal structure including a 4 position and a 17 position and the parent androgen further has a 17β-hydroxy group comprising a 17β-hydroxy oxygen appended to the 17 position and a 17β-hydroxy hydrogen appended to the 17β-hydroxy oxygen.

The method according to this aspect of the invention comprises administering to the subject a compound comprising a substrate and a promoiety. The substrate has the skeletal structure of the parent androgen comprising a 4 position and a 17 position corresponding to the 4 and 17 positions respectively of the parent androgen, and the substrate comprises a carbon—carbon double bond at the 4 position. The promoiety is appended to the 17 position of the substrate as a substitute for the 17β-hydroxy hydrogen of the parent androgen, and comprises an alkylcarbonate ester. The method further comprises converting the compound in vivo into the parent androgen. The subject again preferably but optionally is a human being, and the in vivo conversion thus correspondingly comprises converting the compound into the parent androgen in vivo within the human being.

The substrate has the skeletal structure of the parent androgen. The parent androgen may selected from the group consisting of androst-4-ene-3α,17β-diol, androst-4-ene-3β, 17β-diol, and mixtures thereof. The parent androgen also may be selected from the group consisting of estr-4-ene-3α, 17β-diol, estr-4-ene-3β,17β-diol, and mixtures thereof.

The alkylcarbonate ester promoiety may be as described above.

The compound also may comprise 4-ene diols, for example, such as androst-4-ene-3,17β-diol 17β-alkylcarbonate (e.g., androst-4-ene-3,17β-diol 17β- ethylcarbonate), androst-4-ene-3,17β-diol 3,17β-di(alkylcarbonate) (e.g., androst-4-ene-3,17β-diol 3,17β-di(ethylcarbonate)), estr-4-ene-3,17β-diol 17β-alkylcarbonate (e.g., estr-4-ene-3,17β-diol 17β-ethylcarbonate), estr-4-ene-3,17β-diol 3,17β-di(alkylcarbonate) (e.g., estr-4-ene-3,17β-diol 3,17β-di(ethylcarbonate)), and the like.

In each of the aforementioned methods, the compound administration may comprise peroral administration, pernasal administration, transdermal administration, sublingual administration, and other means. The administration of the compound also may be by combinations of these techniques or approaches. Peroral administration is presently preferred.

As part of the method, the compound administration may comprise complexing the compound with an hydroxypropyl beta cyclodextrin, and/or with an hydroxypropyl gamma cyclodextrin. This is particularly applicable if administered sublingually. The compound administration optionally may further include applying an enteric coating to the compound prior to administering the compound.

When administered orally or sublingually, the compound enters the gastrointestinal ("GI") tract, and ultimately the blood stream. Through more direct methods such as through pernasal, transdermal or intravenous injection, the compound enters directly into the blood stream. In each of the instances, the compound may react to form the parent androgen or a prodrug of the parent androgen.

One limitation of known prodrugs of steriods is that, once they are tranformed into the parent steriod, they are broken down in the body, and particularly in the liver. This breakdown reduces in vivo concentration and bioavailability of the steriod. In the presently preferred embodiments of the invention, the compounds are less prone to such breakdown in the body relative to many known prodrug-type compounds. This in many instances is attributable to the alkylcarbonate ester promoiety, which makes the compound more resistant to hydrolysis and other reactions that inhibit or destroy them in the body. In vivo concentrations thus can be maintained more readily, and bioavailability of the parent androgen can be improved.

The compound preferably would be administered in amounts effective to supplement or increase the concentration of the parent androgen in vivo. The appropriate dosage therefore may take into account natural or otherwise expected variations in steroid concentration, such as the normal daily variations in natural steroid production and consumption, and such as normal variations in in vivo steroid concentrations over days or weeks.

According to a related aspect of the method, the compound may be administered using a dosage given periodically for a maximum of two weeks, followed by a period, for example, of at least two weeks, of non-administration to permit recovery of natural parent androgen production in the subject, for example, to the same baseline level possessed by the subject prior to use of the compound.

This can permit the compound to supplement or increase the concentration of the parent androgen in vivo for an effective period, and then terminate further dosages of the compound as its effectiveness attenuates.

The preferred dosage of the compound will depend upon the specific compound, the subject or class of subject to which it is to be administered, and other factors commonly affecting dosage determinations for this type of composition. In general, the dosage should be such that a sufficient amount of the compound enters the system of the subject and supplements or increases the natural in vivo concentration of the parent androgen.

In accordance with presently preferred versions of the inventive method, the compound administration, particularly when applied to humans, comprises administering the compound in an amount ranging from 1.0 mg to 1 gram per day, more preferably in an amount ranging from 50 mg to 500 mg per day, and even more preferably in an amount ranging from 100 mg to 400 mg per day.

Also as part of the compound administration according to this aspect of the invention, the compound may be administered in a dosage periodically for a maximum of two weeks, followed by at least two weeks of non-administration to permit recovery of natural parent androgen production in the subject.

The compound administration also may comprise administering the compound only in morning-time.

Advantages of the preferred compounds and methods according to the invention flow from the advantageous or desirable effects of the parent androgen, as well as from the increased in vivo concentration and bioavailability of the prodrug and/or the corresponding parent androgen resulting from administration of the compound. Compounds such as the alkyl carbonate ester versions wherein the parent androgen skeletal structure corresponds to 5α-androst-1-ene-3α,17β-diol, 5α-androst-1-ene-3β,17β-diol, and mixtures thereof, 5α-estr-1-ene-3α,17β-diol, 5α-estr-1-ene-3β,17β-diol, and mixtures thereof, 17β-hydroxy-5α-androst-1-ene-3-one, 17β-hydroxyandrost-1,4-diene-3-one, 17β-hydroxyestr-1,4-diene-3-one, 17β-hydroxy-5α-estr-1-ene-3-one, and mixtures thereof, androst-4-ene-3α,17β-diol, androst-4-ene-3β,17β-diol, and mixtures thereof, estr-4-ene-3α,17β-diol, estr-4-ene-3β,17β-diol, and mixtures thereof can provide pro-athletic and anabolic effects. In some instances, they can provide improved immune system efficacy, libido increase and/or mood enhancement as well.

Aspects of the alkylcarbonate ester as described above for the other aspects of the invention apply to the compound according to this aspect as well. A carrier such as those forms noted above also may be used.

EXAMPLE 1

To 10 ml dichloromethane was added 1.0 gram androst-4-ene-3,17-diol and 2.00 equivalents each of ethyl chloroformate and 2,6-lutidine. This was then stirred overnight, diluted with an additional 60 ml of dichloromethane, and filtered. The filtrate was washed twice in a separatory funnel with acidic water, once with neutral water, then dried over sodium sulfate and placed in a freezer at −10 C. for two hours. The resulting white colorless crystals were recovered by filtration, yielding 0.47 grams of androst-4-ene-3,17β-diol 3,17β-di(ethylcarbonate)ester.

Pyridine or triethylamine may be used as alternate bases. Alternate solvents include acetone, acetonitrile, and pyridine.

EXAMPLE 2

A compound according to this aspect of the invention may be made from what in fact is comprised of a combination of compounds according to the invention. About 100 mg of a first component of androst-4-ene-3,17β-diol 3,17β-di(ethylcarbonate) and about 200 mg of a second component of 17β-hydroxy-5α-androst-1-ene-3-one 17β-ethylcarbonate ester are added to a liquid carrier component comprising 2,876 mg of purified water, 2,443 mg of glycerin, 1,847 mg of proplyene glycol, 459 mg of polysorbate, 396 mg of Lecithin, 202 mg of EDTA. 185 mg of vegetable gum, 566 mg of natural flavor blend, 96 mg of sodium benzoate, 96 mg of potassium sorbate, and 96 mg of calcium propionate. The components are stirred to achieve dissolution and thus form the resultant solution. This specific example yields approximately 9,620 mg or about 9 ml of the solution. This solution can be taken by a human subject in daily doses of about 9–18 ml.

EXAMPLE 3

About 150 mg of androst-4-ene-3,17β-diol 3,17β-di (ethylcarbonate) and about 150 mg of 17β-hydroxy-5α-androst-1-ene-3-one 17β-ethylcarbonate ester are added to a liquid carrier component comprising 2,876 mg of purified water, 2,443 mg of glycerin, 1,847 mg of propylene glycol, 459 mg of polysorbate, 396 mg of Lecithin, 202 mg of EDTA. 185 mg of vegetable gum, 566 mg of natural flavor blend, 96 mg of sodium benzoate, 96 mg of potassium sorbate, and 96 mg of calcium propionate. The components are stirred to achieve dissolution and thus form the resultant solution. This specific example yields approximately 9,620 mg or about 9 ml of the solution. This solution can be taken by a human subject in daily doses of about 9–18 ml.

EXAMPLE 4

About 200 mg of androst-4-ene-3,17β-diol 3,17β-di (ethylcarbonate) and about 100 mg of 17β-hydroxy-5α-androst-1-ene-3-one 17βethylcarbonate ester are added to a liquid carrier component comprising 2,876 mg of purified water, 2,443 mg of glycerin, 1,847 mg of propylene glycol, 459 mg of polysorbate, 396 mg of Lecithin, 202 mg of EDTA. 185 mg of vegetable gum, 566 mg of natural flavor blend, 96 mg of sodium benzoate, 96 mg of potassium sorbate, and 96 mg of calcium propionate. The components are stirred to achieve dissolution and thus form the resultant solution. This specific example yields approximately 9,620 mg or about 9 ml of the solution. This solution can be taken by a human subject in daily doses of about 9–18 ml.

EXAMPLE 5

About 150 mg of androst-4-ene-3,17β-diol 3,17β-di (ethylcarbonate) and about 150 mg of 17β-hydroxy-5α-androst-1-ene-3-one 17β-ethylcarbonate ester are added to a liquid carrier component comprising 2,150 mg of purified water, 2,800 mg of glycerin, 2,216 mg of propylene glycol, 459 mg of polysorbate, 396 mg of Lecithin, 202 mg of EDTA. 185 mg of vegetable gum, 566 mg of natural flavor blend, 96 mg of sodium benzoate, 96 mg of potassium sorbate, and 96 mg of calcium propionate. The components are stirred to achieve dissolution. This yields approximately 9,620 mg or about 9 ml of the solution. This solution can be taken by a human subject in daily doses of about 9–18 ml.

EXAMPLE 6

About 150 mg of androst-4-ene-3,17β-diol 3,17β-di (ethylcarbonate) and about 150 mg of 17β-hydroxy-5α-androst-1-ene-3-one 17β-ethylcarbonate ester are added to a liquid carrier component comprising 3,550 mg of purified water, 2,132 mg of glycerin, 1,484 mg of propylene glycol, 459 mg of polysorbate, 396 mg of Lecithin, 202 mg of EDTA. 185 mg of vegetable gum, 566 mg of natural flavor blend, 96 mg of sodium benzoate, 96 mg of potassium sorbate, and 96 mg of calcium propionate. The components are stirred to achieve dissolution. This yields approximately 9,620 mg or about 9 ml of the solution. This solution can be taken by a human subject in daily doses of about 9–18 ml.

EXAMPLE 7

About 100 mg of a first component of estr-4-ene-3,17β-diol 3,17β-di(ethylcarbonate) and about 200 mg of a second component of 17β-hydroxy-5α-androst-1-ene-3-one 17β-ethylcarbonate ester are added to a liquid carrier component comprising 2,876 mg of purified water, 2,443 mg of glycerin, 1,847 mg of proplyene glycol, 459 mg of polysorbate, 396 mg of Lecithin, 202 mg of EDTA. 185 mg of vegetable gum, 566 mg of natural flavor blend, 96 mg of sodium benzoate, 96 mg of potassium sorbate, and 96 mg of calcium propionate. The components are stirred to achieve dissolution and thus form the resultant solution. This specific example yields approximately 9,620 mg or about 9 ml of the solution. This solution can be taken by a human subject in daily doses of about 9–18 ml.

EXAMPLE 8

About 150 mg of estr-4-ene-3,17β-diol 3,17β-di (ethylcarbonate) and about 150 mg of 17β-hydroxy-5α-androst-1-ene-3-one 17β-ethylcarbonate ester are added to a liquid carrier component comprising 2,876 mg of purified water, 2,443 mg of glycerin, 1,847 mg of propylene glycol, 459 mg of polysorbate, 396 mg of Lecithin, 202 mg of EDTA. 185 mg of vegetable gum, 566 mg of natural flavor blend, 96 mg of sodium benzoate, 96 mg of potassium sorbate, and 96 mg of calcium propionate. The components are stirred to achieve dissolution and thus form the resultant solution. This yields approximately 9,620 mg or about 9 ml of the solution, which can be taken by a human subject in daily doses of about 9–18 ml.

EXAMPLE 9

About 200 mg of estr-4-ene-3,17β-diol 3,17β-di (ethylcarbonate) and about 100 mg of 17β-hydroxy-5α-androst-1-ene-3-one 17β-ethylcarbonate ester are added to a liquid carrier component comprising 2,876 mg of purified water, 2,443 mg of glycerin, 1,847 mg of propylene glycol, 459 mg of polysorbate, 396 mg of Lecithin, 202 mg of EDTA. 185 mg of vegetable gum, 566 mg of natural flavor blend, 96 mg of sodium benzoate, 96 mg of potassium sorbate, and 96 mg of calcium propionate. The components are stirred to achieve dissolution and thus form the resultant solution. This specific example yields approximately 9,620 mg or about 9 ml of the solution. This can be taken by a human subject in daily doses of about 9–18 ml.

EXAMPLE 10

About 150 mg of estr-4-ene-3,17β-diol 3,17β-di (ethylcarbonate) and about 150 mg of 17β-hydroxy-5α-androst-1-ene-3-one 17β-ethylcarbonate ester are added to a liquid carrier component comprising 2,150 mg of purified water, 2,800 mg of glycerin, 2,216 mg of propylene glycol, 459 mg of polysorbate, 396 mg of Lecithin, 202 mg of EDTA. 185 mg of vegetable gum, 566 mg of natural flavor blend, 96 mg of sodium benzoate, 96 mg of potassium sorbate, and 96 mg of calcium propionate. The components are stirred to achieve dissolution. This yields approximately 9,620 mg or about 9 ml of the solution. This solution can be taken by a human subject in daily doses of about 9–18 ml.

EXAMPLE 11

About 150 mg of estr-4-ene-3,17β-diol 3,17β-di (ethylcarbonate) and about 150 mg of 17β-hydroxy-5α-androst-1-ene-3-one 17β-ethylcarbonate ester are added to a liquid carrier component comprising 3,550 mg of purified water, 2,132 mg of glycerin, 1,484 mg of proplyene glycol, 459 mg of polysorbate, 396 mg of Lecithin, 202 mg of EDTA, 185 mg of vegetable gum, 566 mg of natural flavor blend, 96 mg of sodium benzoate, 96 mg of potassium sorbate, and 96 mg of calcium propionate. The components are stirred to achieve dissolution. This yields approximately 9,620 mg or about 9 ml of the solution. This solution can be taken by a human subject in daily doses of about 9–18 ml.

It has been noted that the compound may, and in many instances preferably does, comprise or consist of combinations of the compounds described herein and/or recited in the claims. The substrate is described in some instances herein as comprising a double bond at a particular position. Preferably in these instances the substrate includes a double bond in the first carbon ring (A) only at the designated position. The promoiety is described herein above as comprising an alkyl carbonate. Optionally and preferably, the promoiety consists of an alkyl carbonate, such as those identified and/or described herein.

Additional advantages and modifications will readily occur to those skilled in the art. Therefore, the invention in its broader aspects is not limited to the specific details, representative devices and methods, and illustrative examples shown and described. Accordingly, departures may be made from such details without departing from the spirit or scope of the general inventive concept as defined by the appended claims and their equivalents.

What is claimed is:

1. A composition for increasing the concentration of a parent androgen in a subject in vivo, the parent androgen having a skeletal structure including a 1 position and a 17 position and the parent androgen further having a 17β-hydroxy group comprising a 17β-hydroxy oxygen appended to the 17 position and a 17β-hydroxy hydrogen appended to the 17β-hydroxy oxygen, the composition comprising:
    a substrate having the skeletal structure of the parent androgen comprising a 1 position and a 17 position corresponding to the 1 and 17 positions respectively of the parent androgen, the substrate comprising a carbon—carbon double bond at the 1 position, the parent androgen being selected from the group consisting of 5α-androst-1-ene-3α,17β-diol and 5α-androst-1-ene-3β,17β-diol; and
    a promoiety appended to the 17β-hydroxy oxygen of the substrate as a substitute for the 17β-hydroxy hydrogen of the parent androgen, the promoiety comprising an alkylcarbonate ester.

2. A composition as set forth in claim 1, wherein the alkylcarbonate ester has an alkyl chain length of less than 12.

3. A composition as set forth in claim 1, wherein the alkylcarbonate ester is selected from the group consisting of methyl carbonate, ethyl carbonate, propyl carbonate, isopropyl carbonate, butyl carbonate, isobutyl carbonate, t-butyl carbonate, valeryl carbonate, hexyl carbonate, heptyl carbonate, octyl carbonate, nonyl carbonate, decyl carbonate, dodecyl carbonate, undecyl carbonate, dodecyl carbonate, cyclopentyl methyl carbonate, cyclopentylpropyl carbonate, cyclohexyl methyl carbonate, and cyclohexylpropyl carbonate, and mixtures thereof.

4. A composition for increasing the concentration of a parent androgen in a subject in vivo, the parent androgen having a skeletal structure including a 1 position and a 17 position and the parent androgen further having a 17β-hydroxy group comprising a 17β-hydroxy oxygen appended to the 17 position and a 17β-hydroxy hydrogen appended to the 17β-hydroxy oxygen, the compound comprising:
    a substrate having the skeletal structure of the parent androgen comprising a 1 position and a 17 position corresponding to the 1 and 17 positions respectively of the parent androgen, the substrate comprising a carbon—carbon double bond at the 1 position; and
    a promoiety appended to the 17β-hydroxy oxygen of the substrate as a substitute for the 17β-hydroxy hydrogen of the parent androgen, the promoiety comprising an alkylcarbonate ester, wherein the composition comprises 17β-hydroxy-5α-androst-1-ene-3-one-17β-ethylcarbonate.

5. A composition for increasing the concentration of a parent androgen in a subject in vivo, the parent androgen having a skeletal structure including a 1 position and a 17 position and the parent androgen further having a 17β-hydroxy group comprising a 17β--hydroxy oxygen appended to the 17 position and a 17β-hydroxy hydrogen appended to the 17β-hydroxy oxygen, the compound comprising:
    a substrate having the skeletal structure of the parent androgen comprising a 1 position and a 17 position corresponding to the 1 and 17 positions respectively of the parent androgen, the substrate comprising a carbon—carbon double bond at the 1 position: and
    a promoiety appended to the 17β-hydroxy oxygen of the substrate as a substitute for the 17β-hydroxy hydrogen of the parent androgen, the promoiety comprising an alkylcarbonate ester, wherein the composition comprises 5α-androst-1-ene-3,17β-diol 3,17β-di (alkylcarbonate).

6. A composition as set forth in claim 5, wherein the compound comprises 5α-androst-1-ene-3,17β-diol 3,17β-di (ethylcarbonate).

7. A composition as set forth in claim 1, further including a carrier.

8. A composition as set forth in claim 7, wherein the carrier comprises a solid carrier.

9. A composition as set forth in claim 7, wherein the carrier comprises a liquid carrier.

10. A composition as set forth in claim 7, wherein the carrier comprises a semi-solid carrier.

11. A composition as set forth in claim 1, wherein the alkylcarbonate ester comprises methyl carbonate.

12. A composition as set forth in claim 1, wherein the alkylcarbonate ester comprises propyl carbonate.

13. A composition as set forth in claim 1, wherein the alkylcarbonate ester comprises isopropyl carbonate.

14. A composition as set forth in claim 1, wherein the alkylcarbonate ester comprises butyl carbonate.

15. A composition as set forth in claim 1, wherein the alkylcarbonate ester comprises isobutyl carbonate.

16. A composition as set forth in claim 1, wherein the alkylcarbonate ester comprises t-butyl carbonate.

17. A composition as set forth in claim 1, wherein the alkylcarbonate ester comprises valeryl carbonate.

18. A composition as set forth in claim 1, wherein the alkylcarbonate ester comprises hexyl carbonate.

19. A composition as set forth in claim 1, wherein the alkylcarbonate ester comprises heptyl carbonate.

20. A composition as set forth in claim 1, wherein the alkylcarbonate ester comprises octyl carbonate.

21. A composition as set forth in claim 1, wherein the alkylcarbonate ester comprises nonyl carbonate.

22. A composition as set forth in claim 1, wherein the alkylcarbonate ester comprises decyl carbonate.

23. A composition as set forth in claim 1, wherein the alkylcarbonate ester comprises undecyl carbonate.

24. A composition as set forth in claim 1, wherein the alkylcarbonate ester comprises dodecyl carbonate.

25. A composition as set forth in claim 5, wherein the alkylcarbonate ester has an alkyl chain length of less than 12.

26. A composition as set forth in claim 5, wherein the alkylcarbonate ester is selected from the group consisting of methyl carbonate, ethyl carbonate, propyl carbonate, isopropyl carbonate, butyl carbonate, isobutyl carbonate, t-butyl carbonate, valeryl carbonate, hexyl carbonate, heptyl carbonate, octyl carbonate, nonyl carbonate, decyl carbonate, dodecyl carbonate, undecyl carbonate, dodecyl carbonate, cyclopentyl methyl carbonate, cyclopentylpropyl carbonate, cyclohexyl methyl carbonate, and cyclohexylpropyl carbonate.

27. A composition as set forth in claim 5, wherein the alkylcarbonate ester comprises methyl carbonate.

28. A composition as set forth in claim 5, wherein the alkylcarbonate ester comprises propyl carbonate.

29. A composition as set forth in claim 5, wherein the alkylcarbonate ester comprises isopropyl carbonate.

30. A composition as set forth in claim 5, wherein the alkylcarbonate ester comprises butyl carbonate.

31. A composition as set forth in claim 5, wherein the alkylcarbonate ester comprises isobutyl carbonate.

32. A composition as set forth in claim 5, wherein the alkylcarbonate ester comprises t-butyl carbonate.

33. A composition as set forth in claim 5, wherein the alkylcarbonate ester comprises valeryl carbonate.

34. A composition as set forth in claim 5, wherein the alkylcarbonate ester comprises hexyl carbonate.

35. A composition as set forth in claim 5, wherein the alkylcarbonate ester comprises heptyl carbonate.

36. A composition as set forth in claim 5, wherein the alkylcarbonate ester comprises octyl carbonate.

37. A composition as set forth in claim 5, wherein the alkylcarbonate ester comprises nonyl carbonate.

38. A composition as set forth in claim 5, wherein the alkylcarbonate ester comprises decyl carbonate.

39. A composition as set forth in claim 5, wherein the alkylcarbonate ester comprises undecyl carbonate.

40. A composition as set forth in claim 5, wherein the alkylcarbonate ester comprises dodecyl carbonate.

* * * * *